(12) United States Patent
Kluge et al.

(10) Patent No.: US 12,741,106 B2
(45) Date of Patent: Sep. 22, 2026

(54) INSUFFLATOR WITH FILTER LOADING DETECTION DEVICE

(71) Applicant: W.O.M. World of Medicine GmbH, Berlin (DE)

(72) Inventors: Tobias Kluge, Berlin (DE); Fabian Langen, Berlin (DE); Jan-Henrik Carstens, Berlin (DE); Henrik Stier, Berlin (DE)

(73) Assignee: Novanta Medical GmbH, Berlin (DE)

( * ) Notice: Subject to any disclaimer, the term of this patent is extended or adjusted under 35 U.S.C. 154(b) by 581 days.

(21) Appl. No.: 18/137,024

(22) Filed: Apr. 20, 2023

(65) Prior Publication Data

US 2023/0414885 A1 Dec. 28, 2023

Related U.S. Application Data

(60) Provisional application No. 63/337,309, filed on May 2, 2022.

(30) Foreign Application Priority Data

Apr. 20, 2022 (DE) ......................... 102022001357.7

(51) Int. Cl.
*A61M 13/00* (2006.01)
*B01D 35/143* (2006.01)
*B01D 46/00* (2022.01)

(52) U.S. Cl.
CPC ....... *A61M 13/003* (2013.01); *B01D 35/1435* (2013.01); *B01D 46/0086* (2013.01);
(Continued)

(58) Field of Classification Search
CPC .......... B01D 46/0086; B01D 46/44–46; B01D 35/143–1435; B01D 27/101; A61B 2218/008; A61M 1/784; A61M 1/79; A61M 11/003; A61M 2039/0241; A61M 2205/125–126; A61M 2205/707; A61M 2205/75; A61M 2205/7536;
(Continued)

(56) References Cited

U.S. PATENT DOCUMENTS 5,246,419 A 9/1993 Absten
6,585,791 B1 * 7/2003 Garito .................. B01D 46/546 604/35
(Continued)

FOREIGN PATENT DOCUMENTS

DE 102016014980 A1 6/2018
DE 102020002738 A1 11/2021
(Continued)

OTHER PUBLICATIONS

Lake et al. (Tunable Pressure Sensing Applications of a MEMS Buckled Membrane, 2015, National Aerospace and Electronics Conferences (NAECON) (Year: 2015).*
(Continued)

*Primary Examiner* — Stephanie Sebasco Cheng
(74) *Attorney, Agent, or Firm* — McCarter & English, LLP; David J. Silvia

(57) ABSTRACT

The present invention relates to an insufflator having an improved detection of the filter load and evaluation of the data in order to enable a longer service life of the filter or a consistent function.

11 Claims, 3 Drawing Sheets

Figure 1:
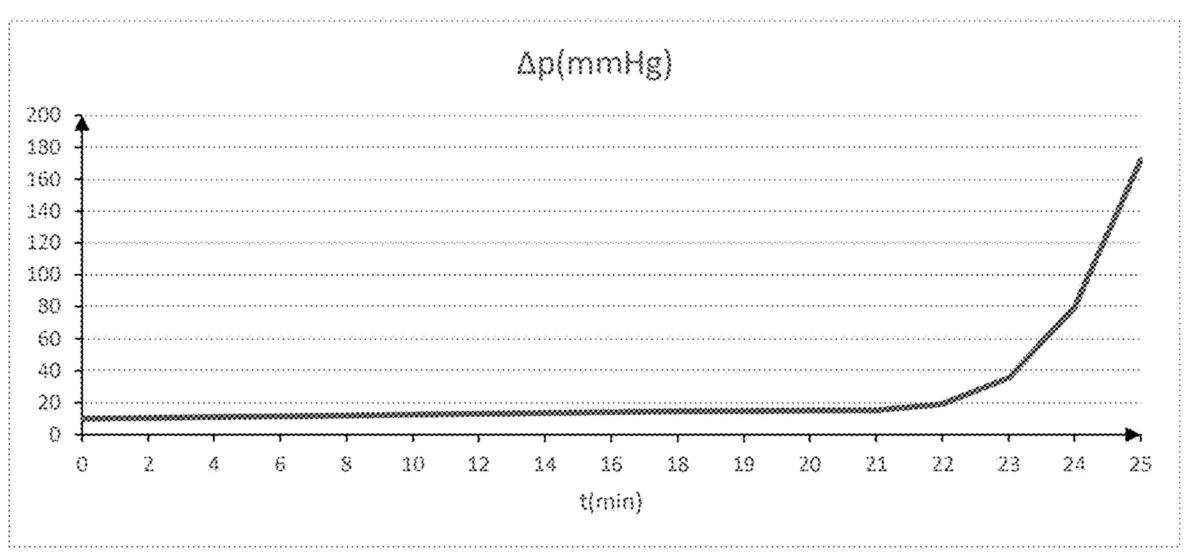
Figure 2:
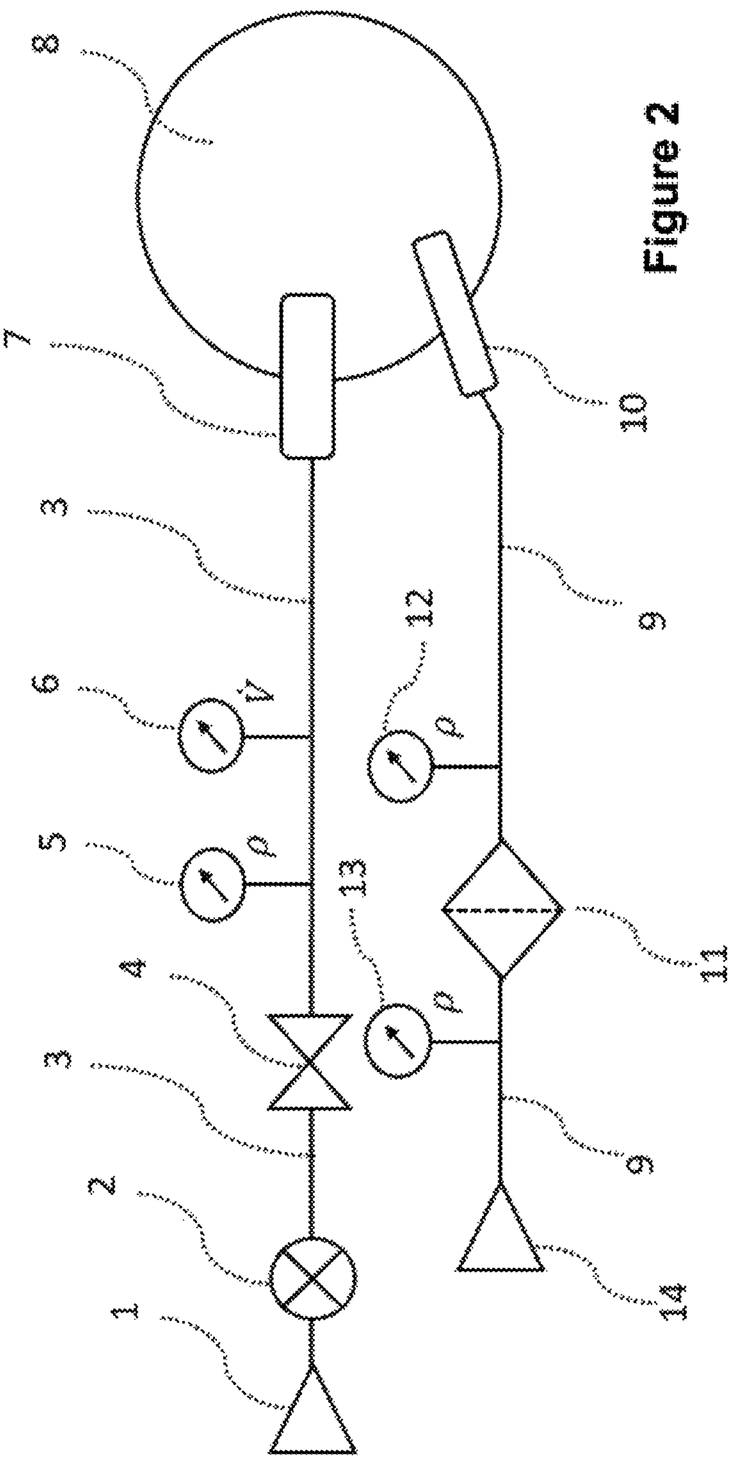

(52) U.S. Cl.
CPC .... *A61B 2218/008* (2013.01); *A61M 2205/18* (2013.01); *A61M 2205/3331* (2013.01); *A61M 2205/502* (2013.01)

(58) Field of Classification Search
CPC .. A61M 2205/7572; A61M 2205/7581; A61M 13/003–006
See application file for complete search history.

(56) References Cited

U.S. PATENT DOCUMENTS

| | | | | |
|---|---|---|---|---|
| 10,546,435 | B2 * | 1/2020 | Carpenter .......... | B01D 46/0002 |
| 2015/0112246 | A1 | 4/2015 | Palmerton et al. | |
| 2019/0201088 | A1 | 7/2019 | Shelton, IV et al. | |
| 2019/0307972 | A1 * | 10/2019 | Koeth ................. | A61M 13/003 |
| 2019/0358567 | A1 * | 11/2019 | Maxwell ........... | B01D 35/1435 |

FOREIGN PATENT DOCUMENTS

| | | | | |
|---|---|---|---|---|
| EP | 3506303 | A1 * | 7/2019 | ............. A61B 18/00 |
| WO | WO 2007050516 | A2 | 5/2007 | |
| WO | WO 2021121462 | A1 | 6/2021 | |

OTHER PUBLICATIONS

Nittmann Kleines Grundbegriffe-Lexikon der Filtertechnick, https:/www.nitmann-filter.de/wissenswertes/grundbegriffe/, Jan. 2, 2022.

PCT International Search Report dated Jul. 26, 2023 for PCT/EP2023/060164.

Examination Report Excerpt of Priority DE 102022001357.6 (no date).

Iriani, Eiji, et al. Developments of Blocking Filtration Model in Membrane Filtration, KONA Powder and Particle Journal, vol. 33, 2016, S. 179-202, ISSN 0288-4534.

www.wikipedia.de “Differenzdrucksensor” Version vom Jun. 7, 2018.

* cited by examiner

INSUFFLATOR WITH FILTER LOADING DETECTION DEVICE

SUBJECT MATTER OF THE INVENTION

The present invention relates to an insufflator with an improved detection of the filter load and evaluation of the data in order to enable a longer service life of the filter or a consistent operation.

PRIOR ART

Insufflators are known from the prior art in manifold configurations. Insufflators usually comprise a tube through which a medical gas is introduced into a body cavity (for example, an abdomen). The gas creates a positive pressure that expands the body cavity to provide sufficient space for the visual inspection or alternatively the therapeutic intervention or the medical intervention. Some embodiments allow for the evacuation of the gas from the body cavity by means of a second tube. These embodiments may also allow a flow of the gas through the body cavity, for example, to supply heated gas and prevent cooling of the patient. More frequently, such embodiments are used, in particular, for therapeutic interventions carried out using electrosurgery or lasers in order to ensure visibility during the intervention and remove waste gases that are harmful to health. For the purpose of conservation of resources, these gases are filtered and fed back in order to compensate for the pressure drop brought about by evacuation and to leave the body cavity expanded.

Furthermore, for the purpose of protecting the health of the user, a filtering of the gas aspirated from the body cavity and which is released into the environment is necessary.

In practice, it has proven to be difficult to configure the filters for an unspecified operational duration. The possibility of dimensioning the filter to be very large so that it can fulfill its filtering effectiveness for a long time is cost-intensive and hindered by a large and heavy filter. A dimensioning using overly small dimensions is problematic, since with progressive use the filter effectiveness decreases, or alternatively the permeability resistance increases. This is expressed by the fact that the visibility deteriorates due to a lack of evacuation capacity.

There is a wide range of solutions for the detection of the filter load based on the differing pressures upstream and downstream of the filter. In this case, the pressure differences that are caused by the permeability resistance which increases with the filter load are evaluated.

US20210207833A1 "Device and method for monitoring HVAC air filter" is a very current application which describes a prediction of the filter load by means of the differential pressure measurement described. The described HVAC filters are technically very similar to the filters used in the insufflator.

In WO2019186501A1 "Method of sensing particulate from smoke evacuated from a patient, adjusting the pump speed based on the sensed information, and communicating the functional parameters of the system to the hub," the evaluation of particulates from smoke for controlling a pumping capacity is described. A functionality with pressure sensors as provided by the solution according to the invention is roughly described in paragraphs [0264] et seq. or alternatively as "example 41," however, this merely as an idea, without any technical teaching, as to when which action leads to the desired result. The control occurs for the smoke-generating medical device (RF generator power request) and paragraph [0282] describes the possibility of generating an alarm. There are, however, no evaluations of pressure measurements being made, but rather there are sensors that determine the particle size and concentration.

Other prior art writings are among others: U.S. Pat. No. 2,927,659A "Dust collector", where the measurement of the pressure differential for detecting the filter load is already described. Methods for monitoring the filter load are furthermore described in: NL2024196B1 "A monitoring system, method and vehicle comprising such a system, for detecting clogging through fouling of an air filter of an internal combustion engine"; EP2960484A1 "System for detecting an air filter condition, in particular for combustion engines" as well as in US11202982B2 "Air filter condition sensing".

A solution is therefore very close to the prior art which provides for an increase of the flow through the expanded body cavity by means of a permeability resistance detected by differential pressure, wherein this differential pressure increases with increasing filter load, this in order to ensure a uniform, patient-friendly expansion. This solution can already be ensured by means of a flow sensor (flow rate sensor) as a sensor and a control for stabilizing the flow rate, wherein in the described case, it is ensured with the method of flow increase controlled by differential pressure that no increased pressure (we are here, in part, dealing with very low pressures around 15 mmHg) is generated in the body cavity, such that the increased evacuation capacity is merely compensated by the increased permeability resistance and is not overcompensated and that leaks do not have any negative influence on the magnitude of the expansion.

It is, moreover, very close to the prior art that by evaluating the differential pressure values over time, a distinction can be made between a loading/occlusion of the filter and the clogging of the filter by means of sudden changes or an evaluation of the first derivation of the pressure values, for example, on the basis of the determination of a threshold value.

A use of the differential pressure or alternatively of a threshold value for the pressure as a warning signal for a filter exchange is likewise disclosed. Following this, an estimation of the remaining service life should be possible.

SOLUTION ACCORDING TO THE INVENTION

In the framework of the development of insufflators, it has been found that the filter systems used for the operation of insufflators show that the detected pressure gradients demonstrate a very specific behavior upon clogging of the filter, namely, initially a slow linear increase of the differential pressure, followed by an exponential increase of differential pressure up until obstruction of the filter. The filter systems used in the insufflator consist of a water-repellent layer, followed by a particle-filtering and a chemically-binding layer, wherein the order of the last two mentioned layers can also be reversed. It is likewise possible that the particle-filtering and the chemically-binding function may be realized in one layer. This pressure gradient over time is represented in an exemplary manner in FIG. 1. The measured pressure loss, which is to say, the difference in pressure of the gas flow upstream and downstream of the filter at a gas flow of 25 L/min, is shown. The pressure loss with a fresh filter amounts to approximately 10 mmHg. The pressure loss increases in a virtually linear manner over time. After approximately 20 minutes, the pressure drop amounts to approximately 15 mmHg.

Thereinafter, the pressure drop increases exponentially and reaches approximately 50 mmHg after approximately 23.5 minutes. A pressure drop of 50 mmHg is no longer acceptable for insufflation. Normally, one would want to avoid pressure differences of more than 35 mmHg. The detection of the onset of the exponential increase in pressure loss is decisive for some embodiments of the invention. It is important to note that even without smoke-producing operation modes, the filters slowly tend to occlusion, presumably due to the inevitable moisture from the expanded body cavities.

Since an interruption of the procedure and a filter change is unavoidable in the case of an overly extensive occlusion and thus an overly high pressure loss, there is a need for a realistic prediction of the remaining service life of the filter.

According to the methods described in the prior art, the prediction as to a service life or alternatively of a remaining service life provides an incorrect, namely surprisingly shortened service life, which can give rise to a critical situation during the course of surgery.

The invention therefore relates to an insufflator for minimally invasive surgery, comprising a) gas connection with proportional valve, b) one first trocar, c) one gas supply line for gas from the gas connection with pressure measurement, filter and connection to the first trocar, d) one evacuation device with adjustable evacuation capacity, e) one second trocar with evacuation hose connected to the evacuation device with adjustable evacuation capacity, f) one filter for cleaning the evacuated gas, which filter is positioned between the second trocar and the evacuation device, h) at least one pressure sensor positioned upstream or downstream of the filter in the direction of the gas flow, i) optionally at least one gas flow sensor, which gas flow sensor is positioned upstream or downstream of the filter in the direction of the gas flow, or at least two gas flow sensors of which at least one is positioned upstream and one downstream of the filter, j) one electronic control unit, k) one display device.

The electronic control unit determines the status of the loading of the filter on the basis of the measured values of the pressure sensors and/or the gas flow sensors, and from this calculates the expected remaining runtime and displays the remaining runtime on a suitable display device.

Furthermore, an alarm is triggered by the electronic control unit when the linear increase of the pressure difference turns into an exponential increase or when the linearly decreasing gas flow turns into an exponentially decreasing gas flow.

In addition, the electronic control unit triggers a signal that prompts the user to temporarily use an operating mode without smoke gas generation when the linear growth of the pressure difference turns to an exponential growth or when the linearly decreasing gas flow turns to an exponentially decreasing gas flow.

According to the invention, the pressure in the evacuation hose is preferably measured upstream and downstream of the filter. The indication of the positions "upstream of the filter" and "downstream of the filter" refers to the flow direction in the evacuation hose. The measurement can be carried out, for example, by at least two gas pressure sensors, of which at least one gas pressure sensor is arranged upstream of the filter and at least one gas pressure sensor downstream of the filter. The pressure difference can be calculated from the measured values and the course of the pressure difference can be monitored over time.

In the simplest case, the course of the occlusion of the filter can also be measured by means of a single gas pressure sensor. With increasing occlusion, at constant inlet pressure and constant gas flow, the pressure upstream of the filter increases, whereas the pressure downstream of the filter decreases. With variable pressure and volume flow conditions, the pressure behavior is more complex, but can be modeled due to the clear correlation between pressure and degree of occlusion. In so doing, even a single gas pressure sensor upstream or downstream of the filter enables a measurement of the occlusion behavior and a calculation of the remaining service life.

According to the invention, the calculated remaining service life of the filter is indicated by a display device. The display device can be integrated in the display of the insufflator or be implemented by an external display device. In each case, an optical and/or acoustic alarm is given for the person carrying out the medical procedure. The relevant limit value for triggering the alarm can be set on the device. By way of example, an initial alarm may be triggered when the linear increase of the pressure differential turns into an exponential increase. Furthermore, a second alarm can be triggered if the pressure difference comes into the critical range (for example, 35-50 mmHg).

The remaining service life can be stabilized with mathematical methods by an evaluation of the determined values, by applying, by way of example, a method for time series analysis or the above-described behavior at the pressure values (linear increase, then transition into exponential increase) is approximated to the measured values by mathematical methods (parameter estimation/curve fit). Thus, according to the invention, differential pressure measurement and evaluation over time will allow for a more accurate prediction of the remaining service life until the filter clogs, as well as other service life extending changes in operating parameters, as described below.

In a further embodiment of the invention, the degree of loading of the filter is determined by means of the gas flow. The gas flow changes over time at constant power of the evacuation pump: as the loading level increases, the gas flow naturally decreases. In the model construction according to FIG. 1, the gas flow at the beginning of the measurements (with fresh filter) is at approximately 23 L/min. After 20 minutes, the gas flow has decreased to approximately 20 L/min. In a manner corresponding to the increase in the pressure difference, this results in a decrease in the gas flow. The gas flow reduction is also initially linear, then later exponential. In the mentioned model construction, after approximately 23 minutes the gas flow has decreased almost linearly to below 10 L/min and thereinafter continues to decrease exponentially.

In a manner similar to the evaluation of the differential pressure, the remaining service life can therefore be determined by a measurement evaluation of the gas flow. The detection of the start of the exponential decrease of the gas flow is decisive for some embodiments of the invention. In a manner thoroughly similar to the embodiments of the invention described above, the alarm may be triggered by means of one or more threshold values, which are naturally dependent on the type of filter used and the expected smoke gas generation. These are determined in advance by measurements. Alternatively, a reasonable remaining service life or alternatively threshold values for triggering an alarm may be specified by the manufacturer or configured by the user and the method of the mathematical methods of time series analysis or parameter estimation described above can be called upon to verify whether these are exceeded by the determined remaining time and to solely enable smoke gas evacuation if this condition is met.

In a step of the invention that goes even further, there is a separate presentation of the remaining service life for normal operating modes (for example, insufflation solely for visual inspection of the abdomen) and smoke gas evacuation (for example, during surgical procedures with electrocoagulation). These are determined separately on the basis of the loading of the filter at a certain point in time in the smoke gas evacuation mode and in the non-smoke gas operating mode. For this purpose, it is necessary that the device recognizes the respective operating mode and adjusts two separate curves for the remaining service life according to the methods already described above and updates them for the respectively active modes. In this manner, the curves of the pressure difference (analogous to FIG. 1) for different operating modes can, for example, be experimentally determined for a determined insufflator with a specific filter. During a procedure, based on the current pressure difference as a measure of the filter loading, the remaining running times for different operating modes can be calculated (for example, 5 min for electrocoagulation or 15 min for visual inspection).

Carrying on, these values or even just one of the values may also be used to create an alarm for changing the filter or the hose set. According to the invention, this would be, for example, if the determined remaining service life of the non-smoke gas evacuation operating modes is less than ¼ of the design service life—and/or the determined remaining service life of the smoke gas evacuation mode is less than 1/10 of the design service life—with other settings being possible depending on the usage scenarios. This alarm would be given for a medical procedure of 15 minutes (design service time) with a remaining service life of less than 3.75 minutes for the non-smoke gas evacuation operating modes and/or less than 1.5 minutes for the smoke gas evacuation mode.

According to the invention, the pressure measurement is pneumatically coupled to the filter. This means a placement of the sensor in the device and a fluidic connection to the measuring site. This presents the advantage that the sterile disposable articles (hose set with filter) make do without electronic components and costs, sterilization and environmental friendliness are positively influenced.

This pneumatic sensor channel must have certain characteristics. The pressure measurement upstream of the filter is carried out with at least one additional sensor, otherwise existing pressure values are used (evacuation pressure, inflow pressure/feeder pressure), which the insufflator requires for the control of the pressure in the body cavity. The sensor channel, which branches off in front of the filter to be observed, also has a filter to prevent partial obstruction or clogging, as this would cause a distortion of the detected pressure values. The diameter must also be in the range of 0.1 to 5 mm so that the pressure can be compensated for quickly.

Figure 3A:
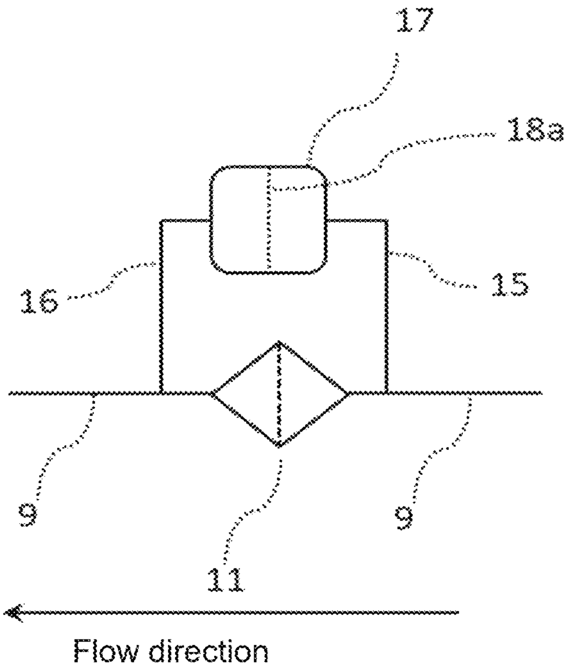
Figure 3B:
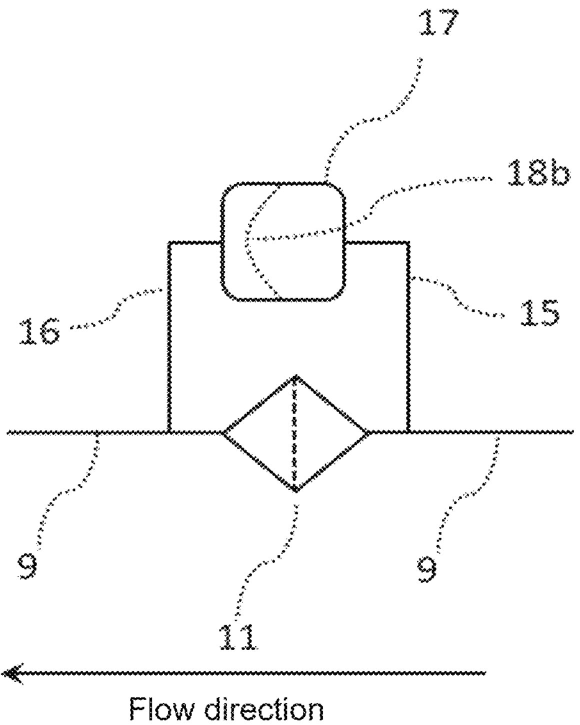

As a further embodiment according to the invention for the detection of the pressure difference, the measuring principle of pneumatically creating a difference by deflecting an elastic membrane and then removing the deflection with a displacement or angle transducer is conceivable. This means that both pressures are diverted to different sides of the filter from the filter housing and guided via channels to the sensor with the membrane and there the deflection is mechanically determined in the device by the pressure difference (FIGS. 3*a/b*). The detection of the deflection of this membrane can, for example, be carried out according to the prior art by mechanical scanning. Alternatively, going beyond the prior art, the deflection of the membrane can also be detected optically, for example by a deflection of a light beam by means of a mirror located on the membrane onto a CCD line, which is to say light-sensitive elements arranged next to each other.

A method for increasing the service life of the filter derived from the pressure measurement according to the invention can be carried out by a pause of the evacuation during the smoke gas generation. This pause can bring about a pressure drop in the cavity, which takes effect after a few minutes, but is quickly compensated in the order of a few seconds. Pauses do not bring about much additional downtime.

An operating mode in which pauses are made in the flow to allow the particles collected in the filter to settle and interrupt the loading of the pores by the pressure of the fluid flow is according to the invention. In so doing, a pulse-pause ratio of 1 minute pause to 10 seconds flow is provided. This increases the service life of the filter, since in this mode a continuation of the medical procedure is possible. An automatic switching into such an operating mode, which can be triggered by a threshold value in the differential pressure is also according to the invention. Carrying on, the existing flow rate (in sLm=standard liters per minute) when the operating mode is activated is evaluated in order to determine the pulse-pause ratios—for example, shorter pauses in the case of greater leaks to minimize a collapse of the expansion. Greater leaks result from the position of the operating point of the control, which is to say, the pairs of values of estimated cavity pressure and the flow introduced into the cavity.

Also according to the invention and more effective is an operating mode in which the user is prompted for a certain period of time to avoid/pause the smoke gas generation (which is to say, laser therapy/HF application/etc.) and after this time once again receives an optical or acoustic signal, that they can once again generate smoke gas. During this time, the insufflator can cause the filter to run dry with an altered, higher flow rate since a humid filter increases the flow resistance in a marked manner. Thereby, an increase or alternatively an extension of the time of a filter effect for the medical procedure or alternatively the filter service life may be achieved. A duration according to the invention would be a few minutes (at least 1.5 minutes, optimally 5 minutes). A flow increase according to the invention would be a doubling of the flow rate, more precisely a flow rate between 5 sLm and 50 sLm. With a flow volume of 5 sLm, a cavity of approx. 5 L volume, as would be the case of the expanded abdomen, would be exchanged once in one minute with unloaded expansion medium and, after the initial exchange, the filter drying effect begins in the next minutes.

A further option according to the invention, when using a humidified and heated hose set is to turn down or switch off the heating for this filter drying operating mode, so that the heat on the humidification medium does not evaporate additional moisture in the body cavity and to then turn the heater back on after the operating mode is completed.

REFERENCE LIST (1) Gas connection
(2) Proportional valve (3) Gas supply line
(4) Volume flow control
(5) Pressure sensor (supply line)
(6) Volume flow sensor (supply line)
(7) First trocar
(8) Cavity
(9) Evacuation hose
(10) Second trocar
(11) Filter
(12) Gas pressure sensor (upstream of filter in flow direction)
(13) Gas pressure sensor (downstream of filter in flow direction)
(14) Evacuation device (adjustable)
(15) Branch line upstream of the filter to the pressure measuring membrane
(16) Branch line downstream of the filter to the pressure measuring membrane
(17) Housing of the pressure measuring membrane
(18*a*) Pressure measuring membrane (neutral, at the same pressure upstream and downstream of the filter)
(18*b*) Pressure measuring membrane (deflected, at higher pressure upstream of the filter)

The invention comprises also a method for operating an insufflator for minimally invasive surgery, comprising a) gas connection with proportional valve,
b) one first trocar,
c) one gas supply line for gas from the gas connection with pressure measurement, filter and connection to the first trocar,
d) one evacuation device with adjustable evacuation capacity,
e) one second trocar with evacuation hose connected to the evacuation device with adjustable evacuation capacity,
f) one filter for cleaning the evacuated gas, which filter is positioned between the second trocar and the evacuation device,
h) at least one pressure sensor positioned upstream or downstream of the filter in the direction of the gas flow,
i) optionally at least one gas flow sensor, which gas flow sensor is positioned upstream or downstream of the filter in the direction of the gas flow, or at least two gas flow sensors of which at least one is positioned upstream and one downstream of the filter,
j) one electronic control unit,
k) one display device.

in particular:

Method for operating an insufflator, wherein the pressure in the evacuation hose is continuously measured upstream and downstream of the filter, wherein the pressure difference is determined from the measured values and wherein the state of loading of the filter is determined from the change in the pressure difference and displayed.

Method for operating an insufflator, wherein an alarm is triggered by the electronic control unit, when the linear increase of the pressure differential turns into an exponential increase or when the linearly decreasing gas flow turns into an exponentially decreasing gas flow.

Method for operating an insufflator, wherein an alarm is triggered by the electronic control unit when the linear increase of the pressure difference turns into an exponential increase as well as optionally a second alarm is triggered, when the pressure difference reaches the critical range (for example, 35-50 mmHg).

Method for operating an insufflator, wherein the remaining service life of the filter is carried out by mathematical methods by an evaluation of the determined values, wherein, for example, a method for time series analysis is applied or the above-described behavior at the pressure values (linear increase, then transition into exponential increase) is approximated to the measured values by mathematical methods (parameter estimation/curve fit).

Method for operating an insufflator, wherein the electronic control unit prompts the user by a signal to pause the flow to allow the particles collected in the filter to settle and to interrupt the loading up of the pores by the pressure of the fluid flow.

Method for operating an insufflator, wherein the electronic control unit triggers an automatic switch-over into an operating mode that permits pauses in the flow.

Method for operating an insufflator, wherein the user is prompted for a certain period of time by a first alarm signal to avoid/pause the smoke gas generation (which is to say, laser therapy/HF application/etc.), and after this time once again receives an optical or acoustic signal that they can once again generate smoke gas.

The invention claimed is:

1. An insufflator for minimally invasive surgery, comprising a) a gas connection with a proportional valve,
b) one first trocar,
c) one gas supply line connected to the first trocar to supply a gas flow from the gas connection to the first trocar, the gas supply line including a pressure measurement device,
d) one evacuation device with adjustable evacuation capacity,
e) one second trocar with an evacuation hose connected to the evacuation device with adjustable evacuation capacity,
f) one filter for cleaning evacuated gas, which filter is positioned between the second trocar and the evacuation device,
g) at least one pressure sensor positioned upstream or downstream of the filter in a direction of the gas flow,
h) the insufflator includes at least one gas flow sensor, which at least one gas flow sensor is positioned up stream or downstream of the filter in the direction of the gas flow, or the insufflator includes at least two gas flow sensors one of which is positioned upstream and one downstream of the filter,
i) one electronic control unit,
j) one display device; and wherein the electronic control unit is configured to control the evacuation device on the basis of measured values from the at least one pressure sensor and/or the at least one or the at least two gas flow sensor(s), to determine a status of a loading of the filter and wherein the electronic control unit is further configured to trigger an alarm when a linear increase of a pressure difference measured by the at least one pressure sensor transitions to an exponential increase or when a linearly decreasing gas flow measured by the at least one or the at least two gas flow sensor(s) transitions to an exponentially decreasing gas flow; and wherein the electronic control unit is further configured to:

calculate and display a first predicted remaining runtime for a smoke-generating operating mode and a second, different predicted remaining runtime for a non-smoke-generating operating mode; and upon triggering of the alarm, provide a signal that prompts a user to temporarily pause the smoke-generating operating mode to enable an extension of filter life.

2. The insufflator according to claim 1, wherein the insufflator is further configured to trigger a signal that prompts the user to temporarily use the non-smoke-generating operating mode when the linear increase of the pressure difference transitions to the exponential increase or when the linearly decreasing gas flow transitions to the exponentially decreasing gas flow.

3. The insufflator according to claim 1, wherein the at least one pressure sensor comprises a gas pressure sensor upstream of the filter in the gas flow direction and a gas pressure sensor downstream of the filter in the gas flow direction, wherein the electronic control unit determines the first and second predicted remaining runtimes on the basis of the measured pressure difference by means of previously empirically determined measurement data.

4. The insufflator according to claim 1, wherein the measured values are evaluated based on a time series analysis and/or a parameter estimation/curve fit to determine the status of the loading of the filter.

5. The insufflator according to claim 1, wherein a change in gas flow is used as a measure of a remaining service life.

6. The insufflator according to claim 1, wherein the at least one pressure sensor is capable of measuring the pressure difference upstream and downstream of the filter by deflection of a membrane.

7. The insufflator according to claim 1, which triggers at least one other alarm if at least one of the first and second predicted remaining runtimes of the filter falls below one or more predetermined time periods.

8. The insufflator according to claim 7, wherein a time period of operation without smoke gas generation amounts to at least 1.5 minutes, preferably approximately 5 minutes at a volume flow of 5 sLm and 50 sLm.

9. The insufflator according claim 1, wherein the filter comprises a plurality of layers, of which at least one layer is a water-repellent layer, at least one layer is a particle-filtering layer and at least one layer is a chemically-binding layer.

10. The insufflator according to claim 1, wherein the filter comprises three layers, wherein the first layer in the gas flow direction is a water-repellent layer, followed in any order by a particle-filtering layer and a chemically-binding layer.

11. The insufflator according to claim 1, wherein the filter comprises a plurality of layers, at least one of which is a water-repellent layer and at least one other of which is a single layer realizing both particle-filtering and the chemically-binding functions.

* * * * *